US012565464B2

(12) United States Patent
Xu

(10) Patent No.: US 12,565,464 B2
(45) Date of Patent: Mar. 3, 2026

(54) PRODUCTION OF ACROLEIN OR ACRYLIC ACID FROM ALLYL ALCOHOL WITH HIGH YIELD AND LOW IMPURITY

(71) Applicant: Rohm and Haas Company, Collegeville, PA (US)

(72) Inventor: Jinsuo Xu, Berwyn, PA (US)

(73) Assignee: ROHM AND HAAS COMPANY, Collegeville, PA (US)

( * ) Notice: Subject to any disclaimer, the term of this patent is extended or adjusted under 35 U.S.C. 154(b) by 739 days.

(21) Appl. No.: 17/632,653

(22) PCT Filed: Sep. 10, 2020

(86) PCT No.: PCT/US2020/050092
§ 371 (c)(1),
(2) Date: Feb. 3, 2022

(87) PCT Pub. No.: WO2021/055220
PCT Pub. Date: Mar. 25, 2021

(65) Prior Publication Data
US 2022/0274905 A1 Sep. 1, 2022

Related U.S. Application Data

(60) Provisional application No. 62/901,995, filed on Sep. 18, 2019.

(51) Int. Cl.
*C07C 45/38* (2006.01)
*C07C 51/25* (2006.01)

(52) U.S. Cl.
CPC ............ *C07C 45/38* (2013.01); *C07C 51/252* (2013.01)

(58) Field of Classification Search
CPC .............................. C07C 45/38; C07C 51/252
See application file for complete search history.

(56) References Cited

U.S. PATENT DOCUMENTS

| | | | |
|---|---|---|---|
| 4,051,181 A | 9/1977 | Murib | |
| 4,107,204 A | 8/1978 | Murib | |
| 4,144,398 A | 3/1979 | Murib | |
| 4,968,846 A | 11/1990 | Kuragano et al. | |
| 6,946,422 B2 | 9/2005 | Stevenson et al. | |
| 2003/0125580 A1 | 7/2003 | Yunoki | |
| 2004/0242926 A1* | 12/2004 | Dieterle et al. ......... C07C 51/16 | |
| | | | 562/545 |
| 2018/0215696 A1 | 8/2018 | Paul et al. | |

FOREIGN PATENT DOCUMENTS

| | | |
|---|---|---|
| CN | 102039143 A | 5/2011 |
| EP | 3015448 | 5/2016 |
| GB | 1184402 A | 3/1970 |
| JP | 2008162907 | 7/2008 |
| WO | 2016167726 A1 | 10/2016 |

OTHER PUBLICATIONS

Ind. Eng. Chem. Prod. Res. Dev. 1984, 23, 393-404 (Grasselli et al.) (Year: 1984).*
JP 2008162907 A (Hiroto et al.; English language machine translation) (Year: 2008).*
Bismuth Molybdate-Based Catalysts for Selective Oxidation of Hydrocarbons; 2018, pp. 181-202 (Le) (Year: 2018).*
ChemSusChem 2012, 5, 1162-1180 (Liu et al.) (Year: 2012).*
JP 2008162907 A (Hiroto et al.; IDS reference; English language machine translation) (Year: 2008).*
Fatiadi, "Active Manganese Dioxide Oxidation in Organic Chemistry" 1976, p. 65.
Kim, "Highly Selective Production of Acrylic Acid from Glycerol via Two Stepts Using Au/CeO2 Catalysts", 2017, vo. 5, p. 11371-11376.
Mannam, "CuCl catalyzed selective oxidation of primary alcohols to carboxylic acids with tert-butyl hydroperoxide at room temperature", 2008, vo. 49, p. 2457.
Murayama, "Role of Crystalline Structure in Allyl Alcohol Selective Oxidation over Mo 3 VO x Complex Metal Oxide Catalysts", 2016, vo. 8, No. 14, p. 2415-2420.
Burrington et al., "Aspects of Selective Oxidation and Ammoxidation Mechanisms over Bismuth Molybdate Catalysts", Journal of Catalysis, 59, 1979; pp. 79-99.
James D. Burrington, et al., "Aspects of Selective Oxidation and Ammoxidation Mechanisms over Bismuth Molybdate Catalysts", Journal of Catalysis, 1980, vol. 63, No. 1, p. 235-254.
Miller et al., "Reaction Pathways in Acrolein Oxidation over a Mixed-Oxide Catalyst", ChemCatChem 10, 2018; 14 pages.
Panov, "Quasi-Catalytic Identification of Intermediates in the Oxidation of Propene to Acrolein over a Multicomponent Bi-Mo Catalyst", published onJanuary 9, 2018, ACS Catalysis, vol. 8, No. 2, pp. 1173-1177.
Jiantai et al., "Molybdenum-based composite oxide catalysts and the kinetics of propylene oxidation", Journal of Lanzhou University (Natural Sciences), 1989(1); 14 pages.

* cited by examiner

*Primary Examiner* — Amy C Bonaparte
*Assistant Examiner* — Derek Rhoades
(74) *Attorney, Agent, or Firm* — CANTOR COLBURN LLP

(57) ABSTRACT

Acrolein is produced by selectively oxidizing allyl alcohol over a first mixed metal oxide catalyst in the presence of oxygen in the vapor phase. The first mixed metal oxide catalyst comprises oxides of molybdenum and bismuth. Acrylic acid is produced by selectively oxidizing the acrolein over a second mixed metal oxide catalyst in the presence of oxygen in the vapor phase. The second mixed metal oxide catalyst has a different composition from the first mixed metal oxide catalyst.

7 Claims, No Drawings

PRODUCTION OF ACROLEIN OR ACRYLIC ACID FROM ALLYL ALCOHOL WITH HIGH YIELD AND LOW IMPURITY

FIELD OF THE INVENTION

The present invention relates to a process for the selective oxidization of allyl alcohol to produce acrolein, and further, the selective oxidization of the produced acrolein to produce acrylic acid.

BACKGROUND OF THE INVENTION

Various processes for preparing acrylic acid are known in the art. Most commercial acrylic acid is produced using fossil fuel based feedstock, such as, for example, propylene.

Acrylic acid can also be made from other starting materials, such as allyl alcohol. However, most commercially available allyl alcohol is also produced from fossil fuel based feedstock. For example, allyl alcohol can be produced from saponification of allyl chloride, which is obtained by chlorination of propylene. Alternatively, allyl alcohol may be produced by the hydrolysis of allyl acetate from the acetoxylation of propylene with acetic acid in the presence of oxygen. Notably, both of these processes require the use of propylene to form allyl alcohol. Therefore, it is more economically feasible to produce acrylic acid directly from propylene rather than use allyl alcohol.

Allyl alcohol can also be produced from biomass derived feedstock, such as glycerol, 1,2-propanediol, or 1,3-propanediol.

Mannan and Sekar disclose that allyl alcohol can be readily oxidized into acrylic acid in liquid phase at room temperature with high efficiency using anhydrous tert-butyl hydroxide in the presence of CuCl catalyst (Mannan and Sekar, Tetra. Lett., 49, 2457 (2008)). A yield of 75% acrylic acid was reported.

Oxidation of allyl alcohol to produce acrylic acid using manganese dioxide was reported with a yield of around 80%. Fatiadi, Syntheses 1976, 65.

Allyl alcohol has also been oxidized in the vapor phase over supported metal catalysts. For example, U.S. Pat. Nos. 4,051,181, 4,107,204, and 4,144,398 reported the use of a bi-metallic catalyst containing palladium and a second metal selected from copper or silver. The combined selectivity to acrylic acid and acrolein reached a percentage in the low 80s, but byproducts propionaldehyde and propionic acid exceeded 5%.

EP 3015448 and Kim and Lee, Sustainable Chem. Eng. 5, 11371 (2017) disclose the oxidation of allyl alcohol to acrylic acid using gold supported on ceria in the liquid phase. The high amount of 3-hydroxypropionic acid byproduct required an additional dehydration step to reduce the yield loss.

Japanese Patent Application Publication JP 2008-162907 and U.S. Patent Application Publication No. 2018/0215696 disclose vapor phase oxidation of allyl alcohol to acrylic acid over a molybdenum/vanadium mixed oxide catalyst. Acrylic acid was produced directly from the allyl alcohol and a high amount of propionic acid was produced. The mass ratio of propionic acid to acrylic acid ranged from 0.014 to 0.85.

Due to the small difference in boiling points of propionic acid and acrylic acid, the removal of propionic acid from acrylic acid is very difficult by distillation. Therefore, it is desirable to minimize the formation of side products such as propionic acid.

It is also desirable to produce acrolein and acrylic acid from biomass derived feedstock.

There is a need for more efficient processes that address one or more of these issues.

SUMMARY OF THE INVENTION

The present invention is directed to methods for preparing acrolein from allyl alcohol, and further, to produce acrylic acid from the acrolein.

According to one aspect of the present invention, a method comprises selectively oxidizing allyl alcohol over a first mixed metal oxide catalyst in the presence of oxygen in the vapor phase to produce acrolein, wherein the first mixed metal oxide catalyst comprises oxides of molybdenum and bismuth.

Another aspect of the present invention comprises further selectively oxidizing the acrolein over a second mixed metal oxide catalyst in the presence of oxygen in the vapor phase, wherein the second mixed metal oxide catalyst has a different composition from the first mixed metal oxide catalyst.

DETAILED DESCRIPTION OF EMBODIMENTS OF THE INVENTION

As used herein, the terms "a," "an," "the," "at least one," and "one or more" are used interchangeably. The terms "comprises," "includes," "contains," and variations thereof do not have a limiting meaning where these terms appear in the description and claims. Thus, for example, a mixture that includes a polymerization inhibitor can be interpreted to mean that the mixture comprises at least one polymerization inhibitor.

As used herein, recitations of numerical ranges by endpoints includes all numbers subsumed in that range (e.g. 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.1 to 100, from 1 to 99.99, from 1.01 to 99.99, from 40 to 6, from 1 to 55, etc.

As used herein, the recitations of numerical ranges and/or numerical values, including such recitations in the claims, can be read to include the term "about." In such instances, the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety or its equivalent U.S. version is so incorporated by reference) especially with respect to the disclosure of definitions (to the extent not inconsistent with any definitions specifically provided in this disclosure) and general knowledge in the art.

One aspect of the present invention relates to a method for producing acrolein from allyl alcohol.

In the inventive process, allyl alcohol is selectively oxidized over a first mixed metal oxide catalyst in the presence of oxygen in the vapor phase.

The first mixed metal oxide catalyst is a solid catalyst comprising oxides of molybdenum (Mo) and bismuth (Bi). The first mixed metal oxide catalyst may also contain at least one additional element selected from iron (Fe), cobalt (Co), nickel (Ni), or combinations thereof. When the first mixed metal oxide catalyst contains at least one additional element, the molybdenum and bismuth are the main metal elements present. Preferably, the first mixed metal oxide catalyst comprises at least 40 wt. % of molybdenum and bismuth based on the total weight of metals in the first mixed metal oxide catalyst, such as, for example, at least 50 wt. %, at least 60 wt. %, or at least 70 wt. %.

The first mixed metal oxide catalyst can be any commercially available catalyst used in the oxidation of propylene to acrolein.

The yield of acrolein based on the allyl alcohol feed is preferably greater than 80% and the mass ratio of propionaldehyde, a byproduct of the reaction, to acrolein is preferably less than 0.001.

Another aspect of the present invention relates to the production of acrylic acid from allyl alcohol. The inventive process for producing acrylic acid from allyl alcohol is a two-step process. In a first step, allyl alcohol is selectively oxidized over a first mixed metal oxide catalyst to form acrolein, as described above.

In a second step, the acrolein is then selectively oxidized over a second mixed metal oxide catalyst in the presence of oxygen in the vapor phase, wherein the second mixed metal oxide catalyst has a different composition from the first mixed metal oxide catalyst.

The second mixed metal oxide catalyst is a solid catalyst that comprises oxides of molybdenum (Mo) and vanadium (V). The second mixed metal oxide catalyst may also contain at least one additional element selected from tungsten (W), copper (Cu), iron (Fe), antimony (Sb), and phosphorus (P). When the second mixed metal oxide catalyst contains at least one additional element, the molybdenum and vanadium are the main metal elements present. Preferably, the second mixed metal oxide catalyst comprises at least 40 wt. % of molybdenum and vanadium based on the total weight of metals in the second mixed metal oxide catalyst, such as, for example, at least 50 wt. %, at least 60 wt. %, or at least 70 wt. %.

The second mixed metal oxide catalyst can be any commercially available mixed metal oxide catalyst used for oxidation of acrolein to acrylic acid.

The yield of acrylic acid based on the allyl alcohol feed is preferably greater than 80%, and the mass ratio of propionic acid, a byproduct of the reaction, to acrylic acid is preferably less than 0.001.

In the selective oxidation reaction to form acrolein and/or acrylic acid, the oxygen can be present in the form of purified oxygen, oxygen in air, or lattice oxygen of the mixed metal oxide catalyst. Preferably, the oxygen is from air or the lattice oxygen of the mixed metal oxide catalyst.

In either the selective oxidation of allyl alcohol to produce acrolein or the selective oxidation of acrolein to produce acrylic acid, steam may be added to assist the reaction.

Purification of the acrolein and/or acrylic acid can be achieved by one or more techniques known in the art, such as, for example, absorption using water or an organic solvent, extraction, fractional distillation, or melt crystallization.

Preferably, the allyl alcohol is produced from a biomass derived feedstock. For example, allyl alcohol can be produced from a biomass derived feedstock such as glycerol, 1,2-propanediol, or 1,3-propanediol.

All living organisms, plant and animal alike, contain a certain amount of carbon-14 ($^{14}C$), which is produced in the atmosphere and fixed by plants during photosynthesis. The ratio of $^{14}C$ to $^{12}C$ ranges from 1 to $1.5\times10^{-12}$. Carbon-14 is a radioactive material having a half-life of around 5700 years. Therefore, biomass derived feedstock contains a ratio of $^{14}C$ to $^{12}C$ similar to that of living organisms, i.e., around 1 to $1.5\times10^{-12}$.

Preferably, the acrolein and/or acrylic acid produced by the process of the present invention comprises a ratio of $^{14}C:^{12}C$ of at least $0.5\times10^{-13}$. More preferably, the acrolein and/or acrylic acid produced by the process of the present invention comprises a ratio of $^{14}C:^{12}C$ of at least $0.75\times10^{-13}$. Even more preferably, the acrolein and/or acrylic acid produced by the process of the present invention comprises a ratio of $^{14}C:^{12}C$ of at least $0.8\times10^{-1}$. Most preferably, the feedstock used in the process of the present invention is entirely sourced from biomass derived material and the ratio of $^{14}C$ to $^{12}C$ is the same as that found in nature, i.e., about 1 to $1.5\times10^{-12}$.

EXAMPLES

The following examples illustrates the present invention but are not intended to limit the scope of the invention.

Example 1—Oxidation of Allyl Alcohol to Acrylic Acid in Two Stages Containing Different Catalysts Allyl alcohol oxidation to acrylic acid was conducted in two stages. First allyl alcohol was oxidized mainly to acrolein in first-stage reactor, in this case a tubular reactor, which is similar to the first stage in a two-stage propylene oxidation process to produce acrylic acid. The catalyst used in the first stage reactor is Mo, Bi-based mixed oxide catalyst, abbreviated as R1 catalyst. In this example 15 ml (15.1 grams) of a Mo- and Bi-based R1 catalyst from Nippon Kayaku Co. (Tokyo, Japan) was mixed with 15 ml of ⅛" Denstone™ 57 beads (Saint-Gobain Norpro, Stow, Ohio), before being loaded into a 2.54 cm (1") outer diameter (OD) stainless steel (SS) first stage tube reactor (0.834" ID).

The product mixture out of the $1^{st}$ stage reactor, abbreviated as R1-Exit, was sent to the $2^{nd}$ stage reactor in ¼" SS tube heated by electrical heating tape. The skin temperature was controlled around 170±10° C.

The $2^{nd}$ stage reactor contains Mo, V-based mixed oxide catalyst, abbreviated as R2 catalyst. In this example 15 ml (15.84 grams) of a Mo, V-based commercial R2 catalyst from Nippon Kayaku Co. (Tokyo, Japan) was mixed with 15 ml of ⅛" Denstone™ beads. The mixture was loaded into the feed inlet side of a U-shaped SS tube with 1" OD and 0.834" OD. The other internal space of the U-shaped tube was filled with Denstone™ beads. The U-shaped tube was put into a fluidized sand bath furnace with the catalyst bed section immersed in the sand bath. The air was used to fluidize the sand at flow rate of 3.3-3.5 SCFM (standard cubic feet per minute). The temperature difference in the bath was controlled no more than 3° C. by maintaining high air flow rate. The bath temperature was adjusted to achieve desired conversion of acrolein to acrylic acid. The effluent from the $2^{nd}$ stage reactor was designated as R2-Exit.

The reactor tube was first heated to 300° C. or higher in a clam-shell electrical furnace in 35.4 ml/min $N_2$ flow. Then 208.3 ml/min of air was added. The values of all gas flow rates were under standard temperature (0° C.) and standard pressure (101.3 kPa) conditions. The allyl alcohol was obtained from Sigma Aldrich with assay above 99%. The allyl alcohol was mixed D.I. water (54.2 wt. % of allyl alcohol) and injected into a SS mixer vessel at rate of 0.114 mi/min when the reactor reached the desired temperature. The residence time of the reactants over the catalyst bed was about 2.7 seconds. The SS mixer vessel was heated to 160-170° C. with the feed air carrying the vapor into the reactor.

The R2-Exit was collected and analyzed. The R2-Exit first flew through Trap 1 which was a 100-500 ml stainless vessel wrapped with ¼" copper coil connected to a recirculation chiller set at 0-1° C. The gases escaping the Trap 1 flew through a second trap, Trap 2, immersed in water/ice, and third and fourth traps (Trap 3A and Trap 3B) immersed in dry ice/iso-propanol mixture. Trap 2 served mainly as a protection trap to prevent high amount of water or acrylic acid getting into a dry ice/iso-propanol trap because water/AA could freeze in dry ice/iso-propanol trap and cause pressure buildup. The trap collection time was typically 2-4

6

$$\text{Yield of product (\%)} = \frac{\text{(moles of the product in R2-Exit)}}{\text{moles of propylene fed}} * 100$$

In case where an empty tube is used as R2 reactor, the R2-Exit is equal to R1-Exit.

The test was conducted with two different reactor temperatures (330 and 340° C.) for the $1^{st}$ stage. The peak temperature (PT) in $1^{st}$ stage catalyst bed was 30-40° C. higher than the reactor temperature (RT). The bath temperature (RT) of the $2^{nd}$ stage reactor was maintained at 310° C. The results are listed in the Table 1. The mass balance of carbon was adjusted to 100% by adjusting the yield of acrylic acid. With almost complete conversion of allyl alcohol, the yield of acrylic acid was above 83%. The yield of propionic acid was very low around 0.02-0.03% which led to the mass ratio of PA/AA 0.00036 or lower.

TABLE 1

Test conditions and yields of products

| Example | Res. T. (sec) | R1 RT/PT (° C.) | R2 RT/PT (° C.) | Conv. (%) C₃H₆O | O₂ | Carbon Mass Balance (%) | COₓ | ACD | PAD | ACR | HOAc | PA | AA |
|---|---|---|---|---|---|---|---|---|---|---|---|---|---|
| Example 1 | 2.7 | 340/375 | 310/331 | 99.9 | 75.2 | 100 | 12.22 | 0 | 0.05 | 0.67 | 3.21 | 0.02 | 83.8 |
| | | 330/364 | 310/331 | 99.96 | 75.7 | 100 | 12.26 | 0 | 0.05 | 0.59 | 3.56 | 0.03 | 83.6 |
| Comparative Example 1 | 2.7 | empty | 287/294 | 23.3 | 21.9 | 98.4 | 4.04 | 0.15 | 2.87 | 9.79 | 0.49 | 1.88 | 10.71 |
| | | | 335/349.5 | 95.7 | 74.4 | 100 | 13.51 | 0.14 | 0.34 | 6.02 | 4.45 | 0.75 | 70.9 |
| Example 2 | 2.7 | 350/383 | None | 100 | 42.5 | 100 | 5.6 | 1.5 | 0.09 | 82.4 | 0.45 | 0.03 | 9.9 |
| | | 330/361 | | 99.96 | 44.1 | 100 | 5.72 | 0.62 | 0.08 | 86.85 | 0.66 | 0.05 | 6.07 |
| | | 310/344 | | 96.5 | 47.2 | 100 | 7.94 | 0.92 | 2.76 | 84.6 | 0.87 | 0.2 | 1.96 |
| | 5.4 | 310/327 | | 99.5 | 47.3 | 100 | 9.22 | 4.35 | 0.81 | 80.7 | 1.38 | 0.31 | 3.55 |

*COₓ = CO + CO₂, ACD = acetaldehyde, PAD = propionaldehyde, ACR = acrolein, HOAc = acetic acid, PA = propionic acid, AA = acrylic acid.

hours. An inhibitor solution of 6-12 grams was injected to Trap 2, Trap 3A and 3B before sample collection to prevent polymer formation. Trap 2 collected very little material most times. 0.2 wt. % of hydroquinone in iso-propanol was used as inhibitor solution.

The off gas from the dry ice/iso-propanol trap was analyzed on-line by a GC equipped with Thermal Conductivity Detector and 5 Å mol-sieve/silica gel column. The main gas components in the off gas typically included nitrogen, oxygen, unreacted propylene, carbon monoxide, and carbon dioxide. The liquids collected from Trap 1 and Trap 2 (if any) were combined into one sample, labeled as T-1 sample. The liquid collected from Trap 3A and Trap 3B were labeled as T-3A and T-3B sample, respectively. The T-1, T-3A and T-3B samples were sent to off-line analysis by a GC equipped with Flame Ionization Detector and a capillary column (DB-FFAP 123-3232E). The conversions of propylene and mass balance of carbon are calculated using the formula below.

Propylene conversion (%)=(moles of propylene fed– moles of propylene inR2-Exit)/moles of propylene fed Carbon mass balance (%)=(total amount of carbon from molecules in R2-Exit including CO₂, CO, propylene, formaldehyde, acetaldehyde, acrolein, acetic acid, propionic acid, acrylic acid)/ (total amount of carbon from propylene fed) *100

The yields of major products or byproducts such as acrylic acid, acrolein, acetaldehyde, propionaldehyde, propionic acid, acetic acid, COₓ (CO and CO₂) after the $2^{nd}$ stage reactor were calculated using the formula below:

Comparative Example 1—Oxidation of Allyl Alcohol in One Step Over Mo, V-Based Oxide Catalyst Allyl alcohol oxidation was conducted in one step over a Mo, V-based oxide catalyst. The experiment was similar to Example 1 except the first stage reactor tube was empty. Allyl alcohol was oxidized directly over commercial R2 catalyst from NK containing Mo and V as main ingredients.

The test was conducted with two different bath temperatures (287 and 335° C.) for the $2^{nd}$ stage reactor. Acrolein was formed along with propionaldehyde at lower temperature besides acrylic acid. Acrylic acid became the main product at higher reaction temperature. The yield of AA reached almost 71% at 95.7% conversion of allyl alcohol at 335 C reactor temperature. However, the AA yield (70.9%) was much lower compared to Example 1 (83.6%). In addition the mass ratio of PA/AA was 0.01 in this case which was ~30 times higher than Example 1.

The results are similar to what reported in U.S. Patent Application Publication No. 2018/0215696 where a mixed oxide containing Mo and V with Fe as optional component. AA yield up to 78.8% was reported with high mass ratio of PA/AA at 0.014 when allyl alcohol was fully converted.

Example 2—Oxidation of Allyl Alcohol to Acrolein

Allyl alcohol can be oxidized mainly to acrolein over a Mo, Bi-based oxide catalyst. The experiment was similar to Example 1 except no $2^{nd}$ stage reaction occurred after the $1^{st}$ stage reactor.

The R1-Exit was collected and analyzed similar to the collection and analysis of R2-Exit in Example 1.

The test results were listed in Table 1. The acrolein yield was adjusted to get carbon mass balance to 100%. Acrolein can be obtained with high yield up to 86% from allyl alcohol oxidation over R1 catalyst. Higher reaction temperature was favored to limit byproduct propionaldehyde.

I claim:

1. A method comprising:

selectively oxidizing allyl alcohol over a first mixed metal oxide catalyst in the presence of water and oxygen in the vapor phase to produce acrolein wherein a mass ratio of propionaldehyde to acrolein is less than 0.001, and selectively oxidizing the acrolein over a second mixed metal oxide catalyst in the presence of oxygen in the vapor phase to produce acrylic acid at a yield of acrylic acid based on allyl alcohol feed of greater than 80% wherein a mass ratio of propionic acid to acrylic acid is less than 0.001;

wherein the first mixed metal oxide catalyst comprises oxides of molybdenum and bismuth; and wherein the second mixed metal oxide has a different composition from the first mixed metal oxide catalyst.

2. The method according to claim 1, wherein the second mixed metal oxide catalyst comprises oxides of molybdenum and vanadium.

3. The method according to claim 2, wherein the second mixed metal oxide catalyst further comprises at least one additional element selected from the group consisting of tungsten, copper, iron, antimony, and phosphorus.

4. The method according to claim 1, wherein the first mixed metal oxide catalyst further comprises at least one additional element selected from the group consisting of iron, cobalt, and nickel.

5. The method according to claim 1, wherein the oxygen is present in the form of purified oxygen, air, or lattice oxygen of the mixed metal oxide.

6. The method according to claim 1, wherein the allyl alcohol is produced from biomass-derived feedstock selected from glycerol, 1,2-propanediol, and 1,3-propanediol.

7. The method according to claim 1, wherein the acrolein has a ratio of $^{14}C$: $^{12}C$ of at least $0.5 \times 10^{-13}$.

* * * * *